United States Patent [19]

Amundson et al.

[11] Patent Number: 4,905,696
[45] Date of Patent: Mar. 6, 1990

[54] METHOD AND APPARATUS FOR P-SYNCHRONOUSLY STIMULATING THE HEART OF A PATIENT

[75] Inventors: Dave Amundson, Boulder, Colo.; Asa Hedin, Stockholm; Kjell Noren, Solna, both of Sweden

[73] Assignee: Siemens Aktiengesellschaft, Berlin and Munich, Fed. Rep. of Germany

[21] Appl. No.: 105,671

[22] Filed: Oct. 7, 1987

[51] Int. Cl.⁴ .............................................. A61N 1/36
[52] U.S. Cl. .......................... 128/419 PG; 128/419 P
[58] Field of Search ................. 128/419 PG, 696, 734, 128/419 PT, 419 P

[56] References Cited

U.S. PATENT DOCUMENTS

| 4,291,699 | 9/1981 | Geddes et al. | 128/419 D |
| 4,535,774 | 8/1985 | Olson | 128/419 PG |
| 4,567,883 | 2/1986 | Langer et al. | 128/696 |
| 4,733,667 | 3/1988 | Olive et al. | 128/419 PG |

FOREIGN PATENT DOCUMENTS 2070282 3/1981 United Kingdom .
2122497 1/1984 United Kingdom .

Primary Examiner—Lee S. Cohen
Assistant Examiner—Scott Getzow
Attorney, Agent, or Firm—Hill, Van Santen, Steadman & Simpson

[57] ABSTRACT

An impedance measurement, used for controlling the pulse generation rate of the pacer, is obtained by placing an electrode in the ventricular portion, rather than the atrial portion, of the heart. The characteristic p-wave in the electrocardiogram is detected as a rapid inflection or notch in the impedance signal, with a stimulation pulse being generated with a time delay following detection of such a notch.

3 Claims, 2 Drawing Sheets

METHOD AND APPARATUS FOR P-SYNCHRONOUSLY STIMULATING THE HEART OF A PATIENT

BACKGROUND OF THE INVENTION

1. Field of the Invention

The present invention relates to a method and a pacer for p-synchronously stimulating the heart of a patient.

2. Description of the Prior Art

Such p-synchronous pacers require a sensing element in the atrium to measure the atrial contraction. This requires, in turn, the use of a separate lead in the atrium or a special ventricular lead with a separate floating electrode in the atrium. Either approach requires a skilled surgeon to successfully implant such a system. It is furthermore subject to sensing problems at a later date.

A p-synchronous pacer as the one referred to above is, for example, described in the Journal "Thoracic and Cardiovascular Surgery", Vol. 46, No. 4 (October, 1963) in an article entitled "Chronic Postsurgical Complete Heart Block" by Lillehei et al. on pages 436–456.

SUMMARY OF THE INVENTION

It is an object of the invention to provide a method and a pacer for p-synchronous heart stimulation which allow for a simpler and more dependable electrical connection with the heart.

According to the present invention a method for p-synchronously stimulating a heart of a patient is provided which comprises the following steps:

(a) placing electrode means in the ventricular portion of the heart;

(b) transmitting a stimulation pulse through said electrode means to said ventricular portion of the heart;

(c) executing an impedance measurement, whereby said impedance includes a vetricular impedance;

(d) generating an impedance signal dependent upon the measured impedance;

(e) detecting a rapid inflection or notch in said impedance signal;

(f) generating a corresponding detection signal;

(g) triggering with a time delay said stimulation pulse, dependent on the occurrence of said detection signal, wherein said time delay corresponds with the atrium-ventricle delay time of the patient's heart.

Further according to the present invention a p-synchronous heart pacer is provided, which comprises:

(a) generating means for generating stimulation pulses;

(b) a pacing electrode means electrically connected with said generating means, said pacing electrode means being designated for being located in the ventricular portion of the heart;

(c) means electrically connected to said pacing electrode means for executing an impedance measurement, whereby said impedance includes a ventricular impedance, and for generating an impedance signal dependent upon the measured impedance;

(d) means for detecting a rapid inflection or notch in said impedance signal and for generating a corresponding detection signal; and (e) means for time-delayed triggering of said means for generating stimulation pulses, dependent on the occurence of a detection signal such that said means for generating stimulation pulses generate a stimulation pulse, wherein the time delay corresponds with the atrium-ventricle delay time of the patient's heart.

Instead of measuring the electric potential evoked by the atrium, the impedance, including the ventricular impedance, is monitored continuously. This impedance measurement indirectly detects the intraventicular volume as one component of the overall body impedance. As the atrium contracts, the ventricular impedance is lowered when the atrial blood enters the ventricle. This results in a rapid inflection (notch) in the overall impedance signal. Thus a signal corresponding to the p-wave can be detected from any ventricular electrode without requiring additional sensing in the atrium. This signal can then be used to trigger the ventricular stimulus (VDD pacing).

The foregoing and other objects, features and advantages of the invention will be apparent from the following more particular description of a preferred embodiment of the invention, as illustrated in the accompanying drawings.

DESCRIPTION OF THE PREFERRED EMBODIMENTS

Figure 1:
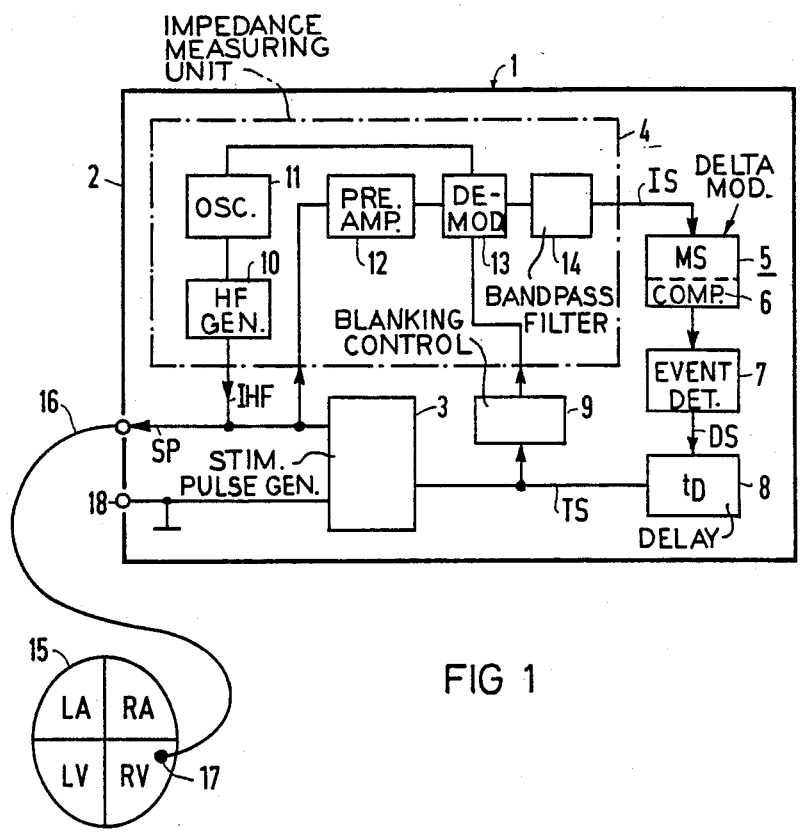
FIG. 1 is a schematic block diagram of a p-synchronous heart pacer according to the principles of the present invention, for a unipolar impedance measurement in the right ventrical of a patient's heart.

In FIG. 1 the p-synchronous pacer 1 comprises a metallic housing 2 encapsulating electrical components. The illustrated components are a stimulation pulse generator 3, which generates stimulation pulses SP, an impedance measuring unit 4, a delta modulator 5, comprising a comparator 6, an event detector 7, a signal delay unit 8, and a blanking control unit 9. The impedance measuring unit 4 includes a high-frequency (e.g. 4 kHz) current generator 10, with oscillator 11, a preamplifier 12, a demodulator 13, which can be blanked by the blanking control unit 9, and a band-pass filter 14 (0,1 Hz–20 Hz).

The signal output of the stimulation pulse generator 3 is electrically connected with the right ventrical RV of the patient's heart 15 through pacing lead 16 and pacing electrode 17. The indifferent electrode (indicated by reference number 18) is formed by metallic housing 2 of the pacer 1. The left ventricle of the heart 15 is indicated with LV. The right and left atriums are indicated by RA and LA, respectively.

According to FIG. 1, a high frequency current IHF is introduced by the high frequency current generator 10 through lead 16 to pacing electrode 17 and, from there, back to indifferent electrode 18 (metallic housing 2 of pacer 1). The current signal received from the body is a measure of the overall impedance between pacing electrode 17, located in the right ventricle, and metallic housing 2 of the pacer (uni-polar impedance measurement). Instead of this unipolar impedance measurement, a bipolar impedance measurement could equally well be used, by locating the indifferent electrode 18, for example, close the the pacing electrode 17 at another point on lead 16, e.g. by fabricating lead 16 as a bipolar catheter. The overall impedance is measured by the elements 12 to 14 of the impedance measuring unit 4. The impedance signal at the output of the impedance measuring unit 4 is generally designated by IS.

In the case of the unipolar system the impedance includes intraventricular (e.g. end systolic, end diastolic volume) and extraventricular components (e.g. respiratory cavitary changes).

For bipolar electrodes this signal is almost entirely due to intraventricular components.

In both cases, there is a characteristic change in the overall impedance resulting from blood entering the atrium from the ventricle. This change appears as a rapid up-down inflection or notch 19 of the overall impedance measurement signal IS (see FIG. 2). Such an inflection 19 is detected by delta modulator 5 in conjunction with event detector 7.

The delta modulator 5 is tuned to a maximum slope, which exceeds less steep non-atrial components of the impedance signal IS. The delta modulator 5, in conjunction with the event detector 7, generates the detector signal DS when a rapid inflection or notch in the impedance signal IS exceeds the maximum slope of the signal MS from the delta modulator 5. This signal DS, which corresponds to the occurance of a p-wave, after a given delay time $t_D$, triggers the stimulation pulse generator 3 to generate a stimulation pulse SP. At the same time it triggers the blanking control unit 9 to blank the demodulator 13 of the impedance measuring unit 4 (blanking time: e.g. 40 ms) while the stimulation pulse SP is generated. The delay time $t_D$ is given by the signal delay unit 8. It corresponds to the atrium-ventricle delay time of the patient's heart (e.g. $t_D = 150$ ms). The trigger signal for triggering the stimulation pulse generator 3 and the blanking control unit 9 is generally designated TS.

Figure 2:
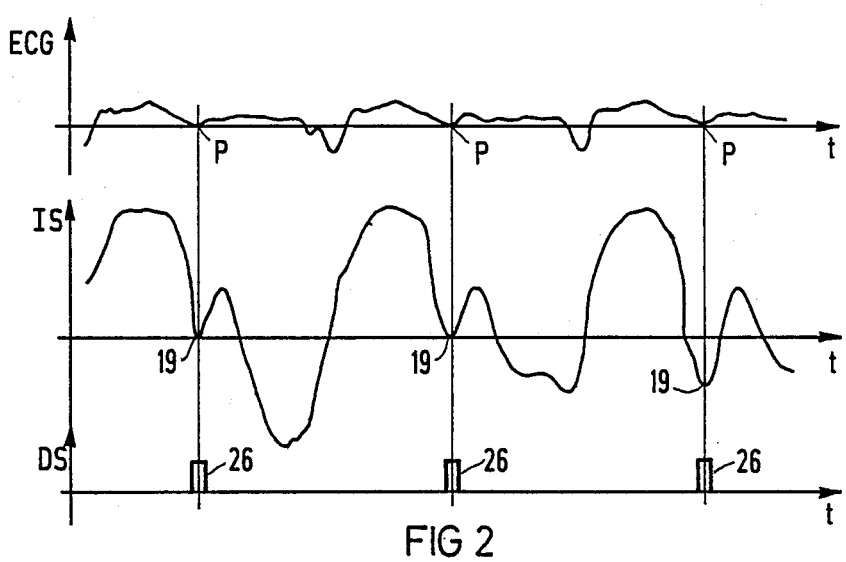
FIG. 2 is an impedance diagram corresponding to an impedance measurement as utilized by the p-synchronous heart pacer according to the principles of the present invention.

In FIG. 2 an electrocardiogram (ECG) comprising p-waves is shown above the impedance signal IS, as a function of time t. As can be seen from FIG. 2, the deflections or notches 19 of the impedance signal IS correspond with the p-waves in the ECG on the time axis.

Figure 3:
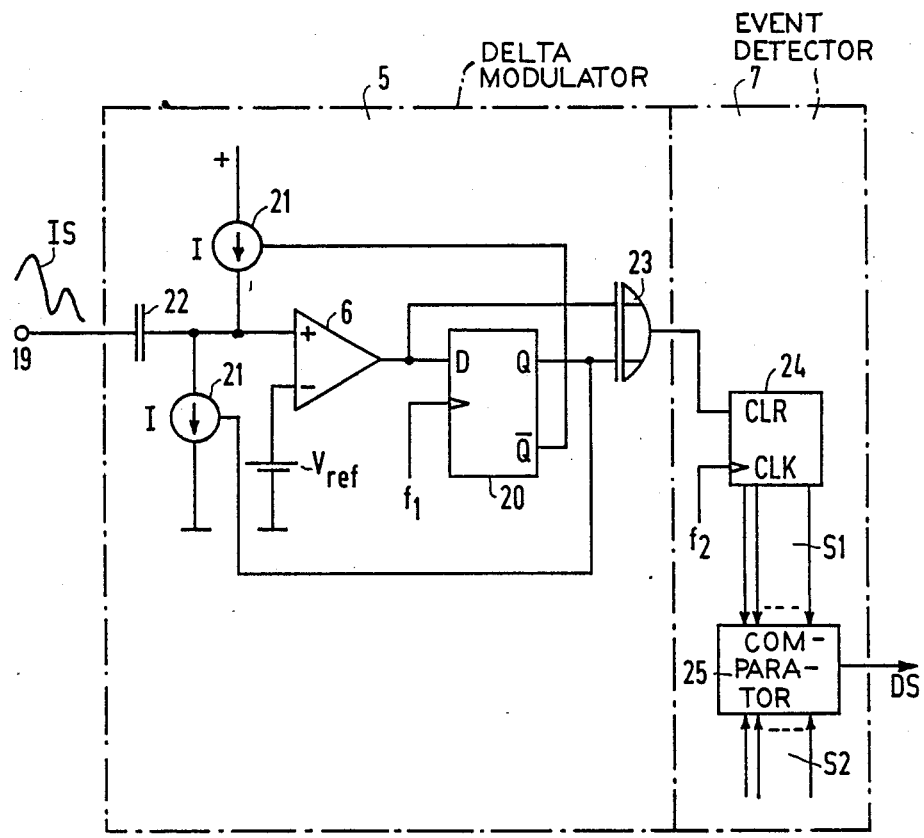
FIG. 3 is a detailed circuit diagram of the delta modulator and the event detector.

In FIG. 3 the delta modulator 5 comprises comparator 6, a bistable multivibrator 20, current generators 21, an integration capacitor 22, and an exclusive-OR-gate 23. The invertinginput of comparator 6 is connected to a reference voltage $V_{REF}$. The bistable multivibrator 20 is clocked by a clock frequency $f_1$ (e.g. 16 kHz). The event detector 7 comprises a counter 24, which is clocked by a frequency $f_2$ (e.g. 4 kHz), and a comparator 25. The comparator 25 compares the output signal $S_1$ of the counter 24 with a time reference signal $S_2$. In case that the output signal $S_1$ meets the time reference signal $S_2$, a detector signal DS is generated.

The operation of the circuit of FIG. 3 is as follows. The impedance signal IS, including inflections or notch 19, is supplied to the delta modulator 5, as indicated in FIG. 3. As soon as an inflection 19 occurs, the opposite side of integration capacitor 22 transfers the signal to the non-inverting input of comparator 6 with a slope of either $+I/C$ or $-I/C$, wherein I is the current of current generator 21 (programmable) and C is the capacity of the integration capacitor 22. Whenever the bistable multivibrator 20 switches from one state to the other, the exclusive-OR-gate 23 zeros the counter 24 in the event detector 7. When the slope of the impedance signal IS exceeds $+I/C$ or falls below $-I/C$ (namely, upon the occurrence of an inflection or notch 19), the bistable multivibrator 20 does not switch. As a result, the time counter 24 of event detector 7 is not zeroed. The output signal $S_1$ of the time counter 24 increases until it meets the time reference signal $S_2$. A detection signal DS is generated, as indicated in FIG. 2, by pulses 26.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims apended hereto.

What is claimed is:

1. A method for p-synchronously stimulating the heart of a patient, comprising the steps of:
   (a) placing electrode means in the ventricular portion of the heart;
   (b) transmitting a stimulation pulse through said electrode means to said ventricular portion of the heart;
   (c) executing an impedance measurement including measurement of a ventricular impedance by transmitting current through said electrode means;
   (d) generating an impedance signal dependent upon the measured impedance, said impedance signal containing a plurality of periodic notches coincident with the entry of arterial blood into the ventricle of the heart;
   (e) detecting said notches in said impedance signal;
   (f) generating a detection signal upon each detection of a notch in said impedance signal;
   (g) triggering a stimulation pulse for supply to said heart with a time delay following the occurrence of said detection signal, said time delay corresponding to the atrium-ventricle delay time of the patient's heart.

2. A p-synchronous heart pacer for stimulating the heart of a patient, comprising:
   (a) generating means for generating stimulation pulses;
   (b) a pacing electrode means electrically connected with said generating means and adapted for location in the ventricular portion of the heart for supplying said stimulation pulses to said ventricular portion of said heart;
   (c) means electrically connected to said pacing electrode means for executing an impedance measurement including measurement of a ventricular impedance, and for generating an impedance signal dependent upon the measured impedance, said impedance signal containing a plurality of periodic notches coincident with the entry of arterial blood into the ventricle of the heart;
   (d) means for detecting said notches in said impedance signal and for generating a detection signal upon the occurrence of each notch; and
   (e) means for time-delayed triggering of said means for generating stimulation pulses, dependent on the occurrence of a detection signal such that said means for generating stimulation pulses generates a stimulation pulse with a time delay corresponding to the atrium-ventricle delay time of the patient's heart.

3. A pacer according to claim 2, wherein said means for detecting said notches comprises a delta modulator tuned to a maximum slope, which exceeds less steep non-atrial components of said impedance signal, and a comparator, which generates said detection signal when a notch in said impedance signal exceeds said maximum slope of an output signal from said delta modulator.

* * * * *